United States Patent [19]

Schmitt et al.

[11] 4,093,555
[45] June 6, 1978

[54] PRODUCTION OF DENTAL MODELS AND TOOTH REPLACEMENT PARTS

[75] Inventors: Werner Schmitt; Robert Purrmann, both of Starnberg; Peter Jochum; Wolf-Dietrich Zahler, both of Hechendorf, all of Germany

[73] Assignee: ESPE Fabrik Pharmazeutischer Praparate GmbH, Seefeld, Germany

[21] Appl. No.: 756,925

[22] Filed: Jan. 4, 1977

Related U.S. Application Data

[63] Continuation of Ser. No. 544,549, Jan. 27, 1975, abandoned.

[30] Foreign Application Priority Data

Jan. 30, 1974 Germany ............... 2404380

[51] Int. Cl.$^2$ .............. C09K 3/00; A61C 13/22; A61C 13/08
[52] U.S. Cl. .............. 252/188.3 R; 106/35; 260/37 N; 260/47 R; 264/19; 260/239 E; 264/17
[58] Field of Search .............. 260/239 E, 47, 37 N; 252/188.3 R; 264/17, 19; 106/35

[56] References Cited

U.S. PATENT DOCUMENTS

| | | | |
|---|---|---|---|
| 3,634,400 | 1/1972 | Schmitt et al. | 260/239 E |
| 3,751,395 | 8/1973 | Schmitt et al. | 260/37 N |
| 3,810,938 | 5/1974 | Schmitt et al. | 106/35 |
| 3,923,740 | 12/1975 | Schmitt et al. | 106/35 |

FOREIGN PATENT DOCUMENTS

| | | | |
|---|---|---|---|
| 1,720,574 | 1/1971 | Germany | 260/239 K |
| 484,977 | 3/1970 | Switzerland | 260/239 K |
| 1,054,635 | 1/1967 | United Kingdom | 260/239 E |

*Primary Examiner*—Benjamin R. Padgett
*Assistant Examiner*—T. S. Gron
*Attorney, Agent, or Firm*—Nolte and Nolte

[57] ABSTRACT

Novel bromine-containing compounds of the formula

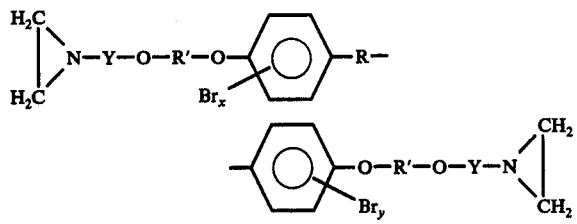

in which R is an alkylidene radical having 1 to 6 carbon atoms, a cycloalkylidene radical or a $SO_2$ radical, R' is an alkylene radical having 2 to 6 carbon atoms or a cycloalkylene radical and Y is an acyl radical of a carboxylic acid having 2 to 6 carbon atoms and optionally bearing an aromatic substituent, and $x$ is 1 or 2 and $y$ is 0, 1 or 2, which are particularly useful for the preparation of dental replacement parts and dental models when mixed with a substance that catalyzes the polymerization of the compounds.

7 Claims, No Drawings

PRODUCTION OF DENTAL MODELS AND TOOTH REPLACEMENT PARTS

This is a continuation of application Ser. No. 544,549, filed Jan. 27, 1975, now abandoned.

For the preparation of dental prosthetics and the like, a model of the jaw as well as of the existing teeth is needed. The model is constituted of a solid mass and must be of the highest accuracy. The material of which the model is constituted should quickly harden in the mold into which it is filled with practically no volumetric change occurring. Additionally, the thus obtained cross-linked polymeric material should not be brittle, because, otherwise, in the fitting of the tooth replacement part a part of the model with which the tooth replacement part is brought into contact can easily break off. Also, it is necessary that the material be mar resistant because in the production of tooth replacement parts the tooth replacement parts must be repeatedly fitted onto the model.

As is known from Swiss Pat. No. 484,977 and German Offenlegungsschrift No. 1,720,574, certain bifunctional ethylenimine compounds are suitable for the production of dental models and tooth replacement parts. Those bifunctional ethylenimine compounds are of the general formula

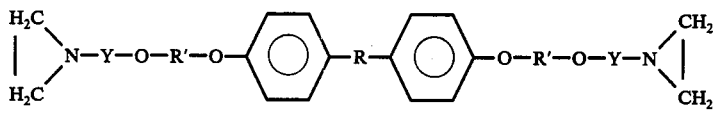

in which R is an alkylidene radical having 1 to 6 carbon atoms, a cycloalkylidene radical or a SO$_2$ radical, R' is an alkylene radical having 2 to 6 carbon atoms or a cycloalkylene radical and Y is an acyl radical of a carboxylic acid having 2 to 6 carbon atoms and optionally bearing an aromatic substituent.

Preferred are those compounds in which R is an isopropylidene group, R' is an alkylene radical having 2 to 3 carbon atoms and Y is an acyl radical having 3 to 4 carbon atoms.

These substances are viscous liquids which can be converted to hard cross-linked products by the addition of a hardening catalyst, such as an alkylating agent or an inorganic or organic acid. These ethylenimine compounds are distinguished by rapid hardening after the addition of the polymerization catalyst at room temperature and by a very slight change in volume effected by the hardening. In the practical production of artificial teeth and other tooth replacement parts or dental prosthetics as well as of dental models, these known ethylenimine compounds are used together with fillers. Suitable fillers are, for example, dispersed silica, barium sulfate and glass fibers of short length and, particularly suitable, are organic polymers, preferably emulsion polymerizates (beads) based on polymethacryl esters and finely pulverized polyamides.

It has been observed that in the storage of mixtures of these bifunctional ethylenimine compounds and fillers for practical use in which for the production of the hardened material it is necessary only to add a hardening catalyst, after some time a separation process occurs by which the filler slowly settles out from the mixture. Consequently, in the withdrawal of the mixture from the container of the apparatus dispensing it, for example, through a tube, for the production of crowns or bridges or the like, there is not always obtained the original, desired proportion of ethylenimine compound and filler in the mixture which is stated by the producer. Moreover, due to greater concentrations of the filler in the lower zones of the storage container undesired pre-cross-linking phenomena are observed. The separating of the mixture is due to the fact that the fillers generally do not have exactly the same specific gravity as the high viscosity liquid ethylenimine compounds.

According to the present invention, it has surprisingly been found that this undesired separating phenomenon and also the pre-cross-linking can be avoided by using as the bifunctional ethylenimine compounds substances in which one or both of the phenylene radicals in the formula given above are substituted with bromine. These new ethylenimine compounds which are substituted with bromine in one or both of the benzene nuclei are of the formula

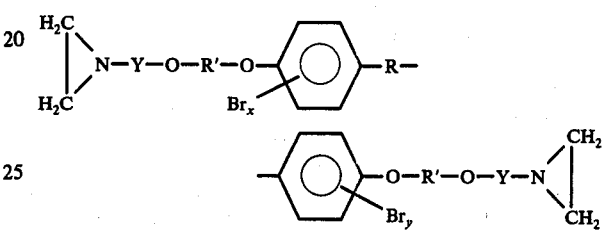

in which R is an alkylidene radical having 1 to 6 carbon atoms, a cycloalkylidene radical or a SO$_2$ radical, R' is an alkylene radical having 2 to 6 carbon atoms or a cycloalkylene radical, —Y—O— is an acyloxy radical of the formula

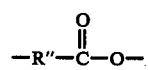

and —O—Y— is an acyloxy radical of the formula

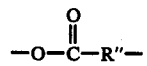

where R" is an alkylene radical having 1 to 5 carbon atoms optionally bearing an aromatic substituent, $x$ is 1 or 2 and $y$ is 0, 1 or 2. The bifunctional ethylenimine compound can, therefore, contain 1 to 4 bromine atoms. Preferably, 2 to 4 bromine atoms are present in the molecule, regardless of whether the bromine atoms are in one or distributed between the two benzene nuclei. The symmetrical compounds are, however, preferred due to the greater simplicity in preparing them. Accordingly, the most preferred compounds are those in which each of the phenylene groups of the molecule contain 1 bromine atom or each of the phenylene groups contain 2 bromine atoms.

These bromine-substituted bifunctional ethylenimine compounds can be used in the same way as the already known afore-mentioned ethylenimine compounds either alone or in mixture with each other or in mixture with other mono- or bifunctional ethylenimine compounds, such other compounds including the aforementioned already known ethylenimine compounds. Through selection of the degree of bromine-substitution the density of the ethylenimine compound can be increased within a relatively wide range. On the other hand, by adding bromine-free ethylenimine compounds the density of the mixture can be so adjusted that it is exactly the same as the density of the filler in question. By the bromination of the phenyl residues in the bifunctional ethylenimine derivatives, not only is the density increased but also the bromination results in an increase of the compression strength of the hardened mass produced from these ethylenimine compounds. By adding a brominated derivative in accordance with the present invention in a weight ratio of 1:2 to an aforementioned known ethylenimine compound there is already observed an increase of 20% in the compression strength of the resultant hardened, cross-linked mass as compared with the compression strength of the product made from the non-brominated ethylenimine compound not mixed with the brominated ethylenimine compound.

The compounds of the invention are generally colorless or weakly yellow colored viscous oils, the viscosity of which is higher than the viscosity of the corresponding bromine-free compounds. By mixing the compounds of the invention with the known bromine-free compounds the viscosity is very much decreased so that, in general, mixtures of the brominated and the unbrominated ethylenimine derivatives will be used. These mixtures are at room temperature sufficiently low in viscosity so that even after addition of the filler they can very easily be worked up. The hardening catalysts can be worked into the mixtures of the invention very easily and quickly and be homogeneously distributed therein so that a problem-free exact processing into the desired tooth replacement part or dental model is possible. As the hardening catalyst there can be used the same compounds as are used for the bromine-free compounds, as disclosed for example in the aforementioned Swiss patent and German Offenlegungsschrift.

The compounds of the invention can be produced in the same way as disclosed for the bromine-free compounds in the aforementioned Swiss patent and German Offenlegungsschrift, however with the use of diphenol derivatives having the desired bromine substitution of the benzene nucleus or nuclei. These brominated diphenol derivatives are well known to those skilled in the art or can readily be made according to known methods in the desired degree of bromination.

Suitable bromine-containing bis-ethylenimine compounds according to the invention for preparing dental models or dental replacement parts include 2,2-bis-(4'-β-hydroxyethoxy-3'-bromphenyl)-propane-bis-α-ethylenimino-butyrate; 2,2-bis-(4'-β-hydroxyethoxy-3'-bromphenyl)-butane-bis-β-ethyleniminobutyrate; 2,2-bis-(4'-β-hydroxypropoxy-3'-bromphenyl)-propane-bis-β-ethylenimino-butyrate; 2,2-bis-(4'-γ-hydroxypropoxy-3'-bromphenyl)-3-methyl-butane-bis-α-ethylenimino-butyrate; 2,2-bis-(4'-β-hydroxyethoxy-3'-bromphenyl)-propane-bis-β-ethylenimino-propionate; 2,2-bis-(4'-γ-hydroxypropoxy-3'-brom-phenyl)-propan-bis-ethylenimino-acetate; bis-(4'-γ-hydroxypropoxy-3'-bromphenyl)-sulfon-bis-β-ethylenimino-butyrate; 2,2-bis-(4'-β-hydroxybutoxy-3'-bromphenyl)-propan-bis-β-ethylenimino-butyrate; 1,1-bis-(4'-β-hydroxyethoxy-3'-bromphenyl)-cyclohexan-bis-β-ethylenimino-butyrate; 2,2-bis-(4'-β-hydroxyethoxy-3'-bromphenyl)-propane-bis-α-ethylenimino-valerianate; 2,2-bis-(4'-β-hydroxyethoxy-3',5'-dibromphenyl)-butane-bis-α-ethyleniminopropionate; 2,2-bis-(4'-γ-hydroxypropoxy-3',5'-dibromphenyl)-propane-bis-α-ethyleniminobutyrate; 2,2-bis-(4'-β-hydroxyethoxy-3',5'-dibromphenyl)-propane-bis-α-ethyleniminobutyrate and 2,2-bis-(4'-β-hydroxyethoxy-3'-bromphenyl)-propane-bis-β-ethyleniminobutyrate.

Together with these compounds the corresponding bromine-free bis-ethylenimine compounds or other known bis-ethylenimine compounds and mixtures thereof can be used for decreasing the relatively high viscosity of the bromine-containing bis-ethylenimine compounds at room temperature.

In the following examples, the new compounds and the use thereof are further described.

EXAMPLE 1

237 g. (0.5 mole) 2,2-bis-(4'-β-hydroxyethoxy-3'-bromphenyl)-propane (melting point 140° C) is heated to boiling for 8 hours with 200 g. (1.2 mole)α-bromobutyric acid in 500 ml. of cyclohexane in the presence of 4 g. of p-toluene sulfonic acid, whereby the water which is formed is continuously removed. After the reaction mixture cools, 500 ml. of ethyl acetate is added thereto and the reaction product is washed several times with aqueous sodium carbonate solution and finally with water. The solvent is distilled, under vacuum in the last stage, and there is thereby obtained 347 g. of 2,2-bis-(4'-β-hydroxyethoxy-3'-bromphenyl)-propane-bis-α-brombutyrate, which can directly be further worked up.

To 280 g. of this substance is added, with stirring, a mixture of 63 g. of ethylenimine, 105 g. of triethylamine and 200 g. of potassium carbonate dropwise, while the temperature is maintained at 20° C. After 15 hours of further stirring at room temperature, the liquid is decanted from the solid residue in the vessel, washed three times with 400 ml. of toluene each time and then the resultant organic solutions are combined and washed repeatedly with water. After the solution is dried with potassium carbonate, the solvent is distilled off, in the final stage under high vacuum. There is thereby obtained 235 g. of a product having an amine equivalent of 358 and an ethylenimine equivalent of 371, which is essentially constituted of 2,2-bis-(4'-β-hydroxyethoxy-3'-bromphenyl)-propane-bis-γ-ethyleniminobutyrate. It has a viscosity at 25° C. of 6120 poises, a specific gravity at 21° C of 1.352 and a bromine content calculated at 23.0% and found to be 22.7%.

To produce a glass-clear model, 1 gram of this dibrominated compound is mixed with 10 mg. of benzene sulfonic acid methyl ester and the mixture is introduced into a mold. The hardening begins after about 1 minute and is essentially completed after about 3 minutes.

EXAMPLE 2

The bis-ethylene compound produced in accordance with Example 1 was mixed in a weight ratio of 1:2 with bromine-free 2,2-bis-(4'-β-hydroxyethoxy-phenyl)-propane-bis-α-ethylenimino-butyrate produced in the analogous way. There is thus obtained an easily flowing mass having a viscosity of 227 poises at 25° C. 500 mg. of this mixture was then stirred with 36 mg. of a mixture constituted of two parts by weight of p-toluene sulfonic acid methyl ester and three parts by weight of 2,3-dibenzyltoluene and the resultant mixture was introduced into a mold. Hardening began after about 2 minutes and was essentially completed after about 6 minutes.

EXAMPLE 3

In order to prepare a mass suitable for the preparation of temporary crowns and bridges, 20 g. of polymethylmethacrylate beads which have been dyed to a toothlike color are stirred into 100 g. of the Example 2 mixture of bifunctional ethylenimine compounds. 6 g. of the thus obtained paste are mixed with 0.35 g. of the same kind of solution of p-toluene sulfonic acid methyl ester as in Example 2. In order to prepare a temporary bridge, the mixture is introduced into an alginate impression of the pillar teeth which was made earlier and in which a deep furrow was cut between the impressions of the pillar teeth, and the impression is then immediately put back into the mouth of the patient. After the beginning of the hardening, the impression together with the hardening molded body is removed from the mouth and permitted to complete hardening for about 10 minutes. Then, in the usual way, the temporary bridge is completed by removal of the excess material and installed on the patient's jaw.

EXAMPLE 4

55 g. of 2,2-bis-(4'-$\beta$-hydroxyethoxy-3',5'-dibromphenyl)-propane (melting point 89°–90° C.) was esterified with 35 g. of $\alpha$-brombutyric acid in the same way as described in Example 1. There was thus obtained 68 g. of the corresponding bis-$\alpha$-brombutyrate, which can be directly further worked up. The melting point after crystallization from ether is 46° to 47° C. 62.4 g. of this substance is reacted in the manner described in Example 1 with 16.1 g. of ethylenimine in the presence of 51 g. of $K_2CO_3$ and 13 g. of triethylamine, resulting in 38 g. of a product having an amine equivalent of 448 and an ethylenimine equivalent of 470, which product is essentially constituted of 2,2-bis-(4'-$\beta$-hydroxyethoxy-3',5'-dibromphenyl)-propane-bis-$\alpha$-ethylen-iminobutyrate. This product has a specific gravity at 23° C. of 1.556 and a bromine content calculated to be 37.5% and found to be 36.9%. 1.0 g. of this tetrabrominated compound was mixed with 10 mg. of p-toluene sulfonic acid methyl ester and immediately introduced into the mold. The cross-linking proceeds very quickly and after a few minutes is completed.

EXAMPLE 5

5.7 g. of the compound produced according to Example 4 is mixed with 23 g. of 2,2-bis-(4'-$\beta$-hydroxyethoxyphenyl)-propane-bis-$\alpha$-ethyleniminobutyrate. There is thus obtained a mixture having a viscosity of 240 poises (25° C.) and a specific gravity of 1.186 (23° C.). 500 mg. of this mixture is combined with 30 mg. of the catalyst solution of Example 2. Hardening begins after about 3 minutes and is essentially completed after about 8 minutes.

EXAMPLE 6

410 mg. of 2,2-bis-(4'-$\beta$-hydroxyethoxy-3'-bromphenyl)-propane is heated to boiling for 20 hours with 223 g. of crotonic acid in 650 ml. of cyclohexane in the presence of 12 g. of p-toluene sulfonic acid and 0.6 g. of 2,6-di-t-butyl-p-cresol whereby water which is formed is removed continuously. The reaction mixture is worked up as in Example 1 and by concentrating the organic solution there is obtained a crystallized precipitate from which residual liquid is withdrawn by vacuum and which is constituted of 401 g. of 2,2-bis-(4'-$\beta$-hydroxyethoxy-3'-bromphenyl)-propane-dicrotonate, melts at about 60° C., and can be reacted without further purification with ethylenimine. To that end, 122 g. of the dicrotonate is melted and is combined at 40° C. with 0.5 g. of triethylamine and 51 g. of ethylenimine. The mixture is permitted to stand for 5 days at room temperature and is then dissolved in 600 ml. of a mixture of cyclohexane and ethyl acetate in which the volumetric ratio of the cyclohexane to the ethyl acetate is 2:1. The organic solution is washed several times with water. After drying of the solution with sodium sulfate and concentrating of the solution, finally under high vacuum, there is obtained 126 g. of a highly viscous substance having an amine equivalent of 374 and an ethylenimine equivalent of 379 which is essentially constituted of 2,2-bis-(4'-$\beta$-hydroxyethoxy-3'-bromphenyl)-propane-bis-$\beta$-ethylenimino butyrate, having a bromine content calculated to be 23.0% and found to be 22.4%. 1.0 g. of this substance is mixed with 25 mg. of p-methoxybenzene sulfonic acid methyl ester and the mixture is introduced into a mold. The hardening begins very soon and is essentially completed after 10 minutes.

EXAMPLE 7

80 g. of the final dibrominated compound produced in Example 6 is mixed with 146 g. of 2,2-bis-(4'-$\beta$-hydroxyethoxy-phenyl)-propane-bis-$\beta$-ethylenimino butyrate. The resultant mixture is of relatively low viscosity and can be worked very easily by hand. 29 mg. of p-toluene sulfonic acid methyl ester is stirred into 1.0 g. of this mixture. Hardening begins after about 3 mins. and is essentially completed after about 8 mins.

EXAMPLE 8

For the production of a mass suitable for the preparation of temporary crowns and bridges 100 g. of the mixture of bifunctional ethylenimine compounds produced according to Example 7 is kneaded with 35 g. of nylon powder as well as 12 mg. of a yellow and 15 mg. of a red pigment. 2.7 g. of the thus obtained paste is then mixed with 30 mg. of benzene sulfonic acid methyl ester, whereafter the paste is used in the same manner as in Example 3.

EXAMPLE 9

For the production of a formulation for the preparation of semi-permanent crowns and bridges for patients having light teeth, 6.6 g. of tooth-colored polymethylmethacrylate beads (made by emulsion polymerization) and 0.12 g. of a white pigment based on zinc sulfide are stirred at 40° C. into 20 g. of the ethylenimine compounds mixture of Example 5. The temporary bridge is prepared in the same way as in Example 3.

COMPARATIVE EXAMPLE

The compression strength of a hardened ethylenimine material is of great significance not only in the use thereof for technical purposes but is even more, significant in the use of the substances of the invention for dental purposes since tooth replacement parts must resist the pressure imposed by chewing. This, of course, includes provisional crowns and bridges, for which the substances of the invention are especially advantageous. To demonstrate this, the novel brominated bifunctional ethylenimine compounds and the ethylenimine compounds of the prior art were experimented with.

There was investigated, on the one hand, the low viscosity mixture described in Example 2 of a dibrominated compound according to the invention with the corresponding bromine-free substance (in the weight ratio of 1:2), and, on the other hand, the following prior art bromine-free compound alone, 2,2-bis-(4'-β-hydroxyethoxy-phenyl)-propane-bis-α-ethylenimino-butyrate. As fillers were used:

(a) tooth colored polymethylmethacrylate beads (20 parts, by weight, to 100 parts, bei weight, of ethylenimine compound);

(b) polyamide powder (O C Merck) (35 parts, by weight, per 100 parts, by weight, of ethylenimine compound).

The hardening of the substances is according to the procedure described in Example 2.

The experiment was carried out on cylindrical test bodies (height 12 mm., diameter 6 mm.), in which the testing was carried out after 24 hours storage in water at 36° C. Test apparatus: Press and Bend Testing Machine Frank Type 581; feed: 4 mm./min. The results obtained were as follows:

|  | Compression strength (kp/cm$^2$) | |
| --- | --- | --- |
| Filler | Mixture of Example 2 | Prior art substance |
| None | 970 | 840 |
| Polymethylmethacrylate | 780 | 680 |
| Polyamide | 710 | 600 |

The results in this table show that the addition of a substance according to the present invention in the proportion of about 33%, by weight, to a prior art substance increases the compression strength about 15 to 20%.

What is claimed is:

1. An homogenous composition suitable for the production of dental replacement parts and dental models comprising a mixture of a bromine containing compound of the formula

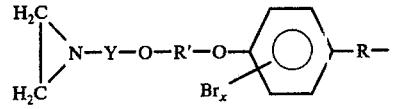

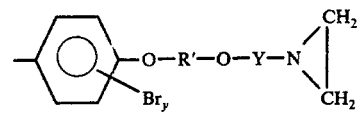

in which R is an alkylidene radical having 1 to 6 carbon atoms, a cycloalkylidene radical or a SO$_2$ radical, R' is an alkylene radical having 2 to 6 carbon atoms or a cycloalkylene radical and —Y—O— is an acyloxy radical of the formula

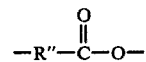

and —O—Y— is an acyloxy radical of the formula

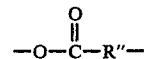

where R" is an alkylene radical having 1 to 5 carbon atoms optionally bearing an aromatic substituent, and $x$ is 1 or 2 and $y$ is 0, 1 or 2; and at least one compound of the group consisting of the bromine-free analogs of the compounds.

2. A composition in accordance with claim 1 wherein the weight ratio of the bromine-containing compound to the bromine-free compound is 1 to 2.

3. A composition in accordance with claim 2 additionally containing a dental filler, the density of said filler being substantially equal to the density of the mixture of the bromine-containing and bromine-free compounds, said filler being an organic filler selected from the group consisting of polymethylmethacrylate beads and polyamide powder.

4. A composition in accordance with claim 1 wherein the bromine containing compound is 2,2-bis-(4'-β-hydroxyethoxy-3'-bromophenyl)-propane-bis-α-ethyleneiminobutyrate.

5. A composition in accordance with claim 1 wherein the bromine-containing compound is 2,2-bis-(4'-β-hydroxyethoxy-3',5'-dibromo-phenyl)-propane-α-bis-ethyleniminobutyrate.

6. A method of making dental replacement parts and dental models comprising disposing the composition of claim 1 and a polymerization catalyst in the configuration of said dental replacement part or dental model and permitting the mixture to polymerize.

7. A method of making dental replacement parts and dental models comprising disposing the composition of claim 3 and a polymerization catalyst in the configuration of said dental replacement part or dental model and permitting the mixture to polymerize.

* * * * *

UNITED STATES PATENT AND TRADEMARK OFFICE
CERTIFICATE OF CORRECTION

PATENT NO. : 4,093,555
DATED : June 6, 1978
INVENTOR(S) : Werner Schmitt et al

It is certified that error appears in the above-identified patent and that said Letters Patent are hereby corrected as shown below:

Column 8, Line 44:

-- propane -$\alpha$- bis -- should read -- propane - bis -$\alpha$ .

Signed and Sealed this

Third Day of April 1979

[SEAL]

Attest:

RUTH C. MASON
Attesting Officer

DONALD W. BANNER
Commissioner of Patents and Trademarks